United States Patent [19]
Newman

[11] Patent Number: 5,368,553
[45] Date of Patent: Nov. 29, 1994

[54] INVISIBLE BANDAGE ASSEMBLY

[76] Inventor: Nancy M. Newman, 819 Spring Dr., Mill Valley, Calif. 94941

[21] Appl. No.: 964,339

[22] Filed: Oct. 21, 1992

Related U.S. Application Data

[63] Continuation-in-part of Ser. No. 729,463, Jul. 12, 1991, abandoned.

[51] Int. Cl.⁵ .................. A61F 13/00; A61F 15/00; A61L 13/00
[52] U.S. Cl. .................. 602/58; 602/41; 602/42; 602/54; 602/48; 602/304
[58] Field of Search .................. 206/570, 581; 602/41-52, 54-59; 604/304, 307

[56] References Cited

U.S. PATENT DOCUMENTS

| | | |
|---|---|---|
| 2,553,270 | 5/1951 | Parrott . |
| 3,297,034 | 1/1967 | Peavy .................. 604/307 |
| 3,645,835 | 2/1972 | Hodgson . |
| 3,687,136 | 8/1972 | Carmody . |
| 4,202,925 | 5/1980 | Dabroski . |
| 4,499,896 | 2/1985 | Heinecke . |
| 4,561,435 | 12/1985 | McKnight et al. .................. 604/304 |
| 4,616,644 | 10/1986 | Saferstein et al. . |
| 4,687,476 | 8/1987 | Pailin . |
| 4,730,611 | 3/1988 | Lamb .................. 602/46 |
| 4,793,003 | 12/1988 | Riedel et al. . |
| 4,875,473 | 10/1989 | Alvarez . |
| 4,909,244 | 3/1990 | Quarfoot . |
| 4,998,617 | 3/1991 | Ladd, Jr. et al. . |
| 5,117,981 | 6/1992 | Crawford et al. .................. 206/570 |

Primary Examiner—Randall L. Green
Assistant Examiner—P. Zuttarelli
Attorney, Agent, or Firm—Morrison & Foerster

[57] ABSTRACT

A bandage assembly for concealing a skin wound, blemish or other dermatologic condition comprising: a segment of adhesive tape that is sized and shaped to overlie the site of the wound, blemish or condition and which has a top surface and a periphery; and a layer of make-up that matches the color of the skin and covers the top surface and periphery of the tape and the area of skin immediately surrounding the segment and is smoothed or feathered at its edge to blend with the skin.

19 Claims, 3 Drawing Sheets

INVISIBLE BANDAGE ASSEMBLY

CROSS-REFERENCE TO RELATED APPLICATION

This application is a continuation-in-part of U.S. application Ser. No. 729,463 filed 12 Jul. 1991 now abandoned.

DESCRIPTION

1. Technical Field

This invention is in the medical and cosmetic fields. More specifically, it concerns bandages useful for a variety of medical applications and as dermatologic cover-ups. Still, more specifically, it relates to bandages which are not readily apparent to an observer, that is, "invisible" as that term is defined herein.

2. Background of the Invention

There are many commercially available types of bandages of different shapes and sizes, most of which are monochromatic—of a beige color that is apparently designed to match the skin tone of certain Caucasians. Exemplary of such bandages are BAND-AID TM Sheer Bandages [Johnson & Johnson Products Inc.; New Brunswick, N.J. (U.S.A.)].

Also available commercially are a spray-on adhesive-type of bandage, for example, plastic spray-on bandages. Such spray-on bandages produce a relatively transparent cover which is generally occlusive and tends to dry and crack.

There is a need in the art for bandages which can be used to perform medical functions in a cosmetically acceptable manner and/or to provide coverage for unsightly dermatologic conditions. This invention fulfills that need and further meets other requirements that are desirable for cover-ups and wound dressings.

The "invisible bandages" of this invention are flexible and conform to the contours of the section of the body to which they are to be applied, and when medically appropriate, have a specified degree of occlusivity and/or are non-adherent to wounds. The invisible bandages of this invention are not only designed to be cosmetically acceptable and comfortable, but also can be used to promote wound healing and provide vehicles for applying a variety of medicaments. Rather than being monochromatic, the invisible bandages of this invention are designed to match the skin of the individual to whom the bandage is to be applied, no matter what color the individual's skin is.

DISCLOSURE OF THE INVENTION

One aspect of the invention is a bandage assembly for concealing a section of skin on a person comprising (a) a segment of adhesive tape attached to the skin over said section, said segment having a top surface and a periphery; and (b) a layer of make-up having a coloration that matches the coloration of said section, said layer covering said top surface and periphery of the tape and the skin outwardly adjacent said periphery, thereby concealing said section and the segment of adhesive tape.

Another aspect of the invention is a method of concealing a section of skin on a person comprising affixing a segment of adhesive tape over said section, said segment having a top surface and a periphery, and covering the top surface and periphery of the segment of adhesive tape and the skin outwardly adjacent said periphery with a layer of make-up having a coloration that matches the coloration of the skin, thereby concealing said section and the segment of tape.

BRIEF DESCRIPTION OF THE DRAWINGS

In the drawings, which are not to scale.

In the drawings like parts or elements are referred to by the same reference numerals.

DETAILED DESCRIPTION OF THE INVENTION

Figure 1:
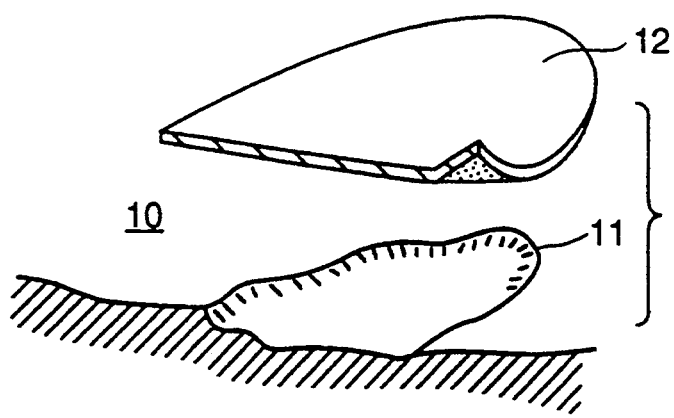
FIG. 1 is a sectional plan exploded view of a skin wound and a segment of adhesive tape adapted to cover the wound.

This invention provides for cosmetically acceptable wound/blemish covers which conform to skin contours and surfaces, are porous to promote healing and can, if medically appropriate, provide a therapeutic environment in which a wound can heal or a blemish, such as a pimple, can speedily recede. Such covers are herein termed "invisible bandages" wherein that term is defined within the context of this invention as bandage assemblies that are not readily apparent to an observer in that they blend with the skin of the person to whom they are applied and have a feathered edge that makes the transition between the assembly and the skin less discernible.

The invisible bandages match the skin of the person to whom they are applied in that the make-up is selected to match the skin appearance (color, texture, reflectivity) and applied to the bandage in such a manner as to camouflage the bandage. The matching make-up can be any type of make-up including liquid, cream or stick types, provided they have the flowability and malleability to be able to be spread to effectively cover the underlying adhesive tape. Ideally, the make-up is non-greasy, non-smearable, matches the appearance of the skin to which it is applied (i.e., closely resembles the skin in coloration, texture or finish, and reflectivity), is sterilizable, and retains its appearance on both skin and the underlying adhesive tape upon drying and aging. Opaque make-ups having such characteristics may be obtained from commercial sources or custom formulated. They will typically contain vehicles, solvents, emollients, pigments, surfactants, and reflective materials. Examples of commercially available make-ups are those manufactured by Revlon, Inc., Charles of the Ritz Group, Ltd., Noxell Corp., Estee Lauder, and Orlane. "Cover-up" cosmetics such as DERMABLEND TM cosmetics and COVERMARE TM cosmetics may also be used. As used herein, the term "match" is not limited to identity of appearance but intends to include make-ups that closely resemble the skin appearance.

There are many different embodiments for the invisible bandages of this invention. The invisible bandages can be made in any shape to conform to the contours of the surface and site to which they are to be applied.

They are flexible, porous and have a low potential for sensitization. They can be modified to provide therapeutic environments for wound closure and healing.

However, for some uses wherein a wound, such as an abrasion, tissue rupture or surgical opening, is not present, thinness of the bandage assembly may be a very important criterion to maximize the cosmetic acceptability of the bandage. For example, it may be desired to conceal the presence of a scar, keloid or birthmark. For such uses among others, a representative invisible bandage of this invention comprises an adhesive tape, preferably a paper tape, more preferably a micropore-type of paper tape to which is applied a make-up that matches the skin tone of the person to whom the assembly is applied. It is preferred that the tape be applied first and that the make-up then be applied over the tape and blended around it such that both the underlying skin and the tape are concealed.

The tape used for the bandages of this invention can be any kind of tape that can be applied to skin without harm, for example, surgical tape. The tape for the invisible bandages of this invention are those tapes which are preferably flexible and have a texture that retains the cosmetic cover, preferably a paper tape. The paper tape is preferably a micropore-type of paper tape. Examples of paper types useful in this invention are SCAN-POR TM surgical tape [distributed by Allerderm Labs, Mill Valley, Calif. (U.S.A.)] and 3M 1529 paper tape. It has been found that the tackier the tape is, the better it is as a component of the invisible bandages of this invention.

Another preferred representative embodiment of the invisible bandages of this invention is one that comprises in addition to the tape, preferably paper tape, more preferably a micropore-type of paper tape to which the matching make-up is applied, a thin layer of a non-adhesive material that underlies a central portion of the paper tape, for example SUCH TM [Kendall Company, Boston, Mass. (U.S.A.)]. The non-adhesive layer prevents the tape from sticking to the surface of a wound, lesion, abrasion or dermatologic eruption, and thereby promotes the healing process by presenting a non-disruptive surface. It also makes the tape occlusive or semi-occlusive (i.e., it is permeable to gases, impermeable to pathogens, and has limited permeability to water vapor).

Another preferred representative embodiment of the invisible bandages of this invention comprises the adhesive tape, preferably paper tape, more preferably a micropore-type of paper tape to which the matching make-up is applied, a thin layer of non-adhesive material, and in addition, a middle layer between the tape and non-adhesive material, wherein said middle layer comprises an absorptive material and/or materials, such as GORTEX TM [W. L. Gore & Assoc, Elkton, Md. (U.S.A.)], which are air permeable but permeable to liquids and vapors in varying degrees. The absorptive material, for example surgical gauze, gel or hydrocolloid, can be impregnated with medicaments, alone or in combination, that promote wound healing, for example, epidermal growth factors, steroids, antibiotics, hormones and other healing factors that promote therapeutic environments. Exemplary of such medicaments is a topical gel such as a formulation of Slindamycin phosphate, or a drying lotion such as that produced by Halina Andre Ltd. [Austin, Tex. (U.S.A.)].

In certain types of wounds, a moist environment for healing is desirable- In such cases, the absorptive material in the middle layer of the invisible bandage may be air permeable but not particularly liquid permeable. Alternatively, the middle layer may comprise a material such as GORTEX TM which is permeable to air but only in varying degrees permeable to liquids and vapors and is impermeable to pathogens such as bacteria, either alone or in combination with an absorptive material.

Another representative embodiment of the invisible bandages of this invention would be that wherein the non-adhesive layer is not required or is not preferred. For example, a preferred environment for healing may require that an absorptive material impregnated with an appropriate medicant be directly in contact with the wound, abrasion or dermatologic eruption. One embodiment to meet that requirement would be that wherein the invisible bandage comprises tape, preferably paper tape, more preferably a micropore-type of paper tape to which the matching make-up is applied and absorptive material which is appropriately impregnated and upon application of the bandage would be in direct contact with the patient's skin. Another embodiment of this invention which would meet the same requirement is that wherein a material, such as GORTEX TM, which is air permeable but permeable to liquids and vapors in varying degrees, is located in between the tape and an absorptive material layer that is impregnated with a liquid medicament. Thus, in that latter embodiment, the absorptive material would be directly in contact with the skin's surface supplying a therapeutic environment for whatever dermatologic condition is present which environment is further maintained by the presence of the air but variably liquid impermeable material just above the absorptive material.

A still further representative embodiment of this invention is that wherein the invisible bandage comprises tape, preferably paper tape, more preferably a micropore-type of paper tape to which the matching make-up is applied and a material, such as GORTEX TM, which is air permeable but variably liquid impermeable. Such an embodiment would be preferred wherein a moist environment is desirable for the dermatologic condition, but topical applications are not necessary or are not preferred.

In another embodiment of the invisible bandages of this invention, medicaments, such as antibiotics, epidermal growth factors, drying lotions among others, are added to the matching make-up, preferably wherein the make-up is of a liquid type. For example, in such an embodiment, the invisible bandage could comprise an appropriate type of tape and make-up to which has been added the appropriate medicament or medicaments. Another version of such an embodiment wherein the make-up contains a therapeutic agent is that which comprises an appropriate type of tape and a layer of absorptive material, such as surgical gauze, gel or hydrocolloid; whereas still another version would further compromise another thin layer of a non-adhesive material that would be in contact with the patient's skin. Of course, in such an embodiment wherein the make-up is liquid and contains one or more therapeutic agents, it would not be preferred for the invisible bandage to comprise a layer of material that is particularly liquid impermeable.

The drawings further illustrate specific embodiments of the bandage assembly of the invention.

FIGS. 1-4 depict one embodiment of the bandage assembly of the invention and the procedure by which the assembly of the invention is applied to the skin.

Figure 2:
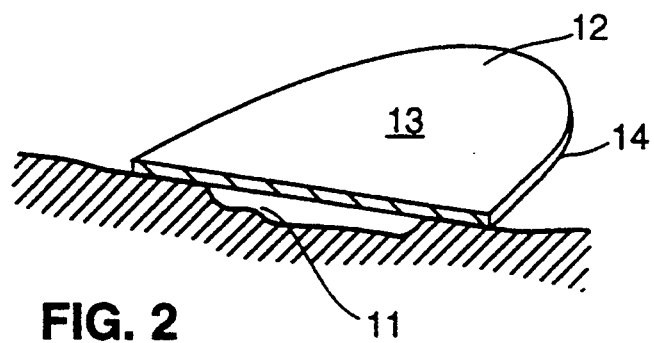
FIG. 2 is a sectional plan view of the wound covered with the tape.
Figure 3:
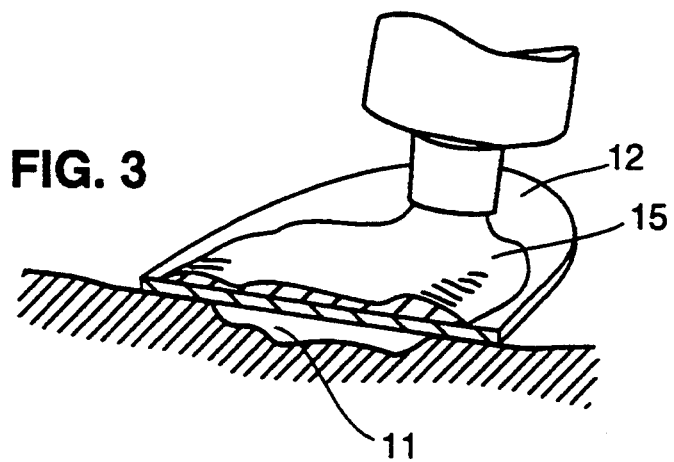
FIG. 3 is a sectional plan schematic view showing make-up being applied to the top face surface of the tape.
Figure 4:
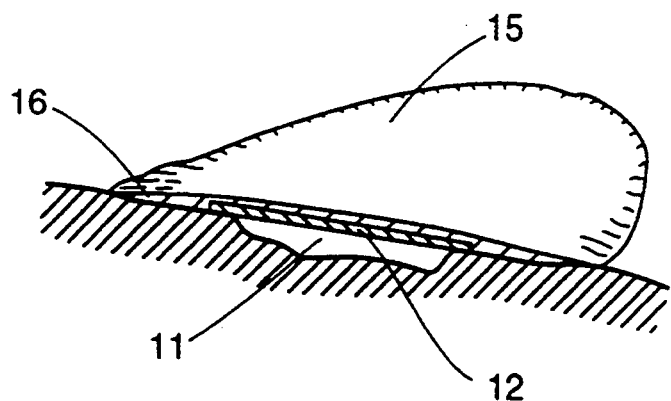
FIG. 4 is a sectional plan view of the wound covered with the tape and make-up.

FIG. 1 shows a section of human skin, designated 10, that has a wound 11 in it. A segment of adhesive tape 12 that is sized and shaped to overlie the wound is placed over the wound as shown in FIG. 2. Such occlusion of the wound protects the wound and promotes healing. The segment has a top surface 13 and a periphery 14. A flowable or malleable make-up formulation, designated 15 in FIGS. 3 and 4, is applied to the top surface as shown in FIG. 3 and then is spread to cover the periphery of the tape segment and the area of skin immediately surrounding the periphery. As shown in FIG. 4 the make-up is smoothed and feathered in the area 16 outwardly of the periphery at a downward (toward the skin) angle from the periphery, so as to lessen the visibility of the transition, junction or edge between the make-up and the skin. As indicated, the appearance (coloration, texture, reflectivity) of the make-up is chosen to match the appearance of the skin. Such matching and the edge feathering of the make-up serve to conceal the assembly from casual observation.

Figure 5:
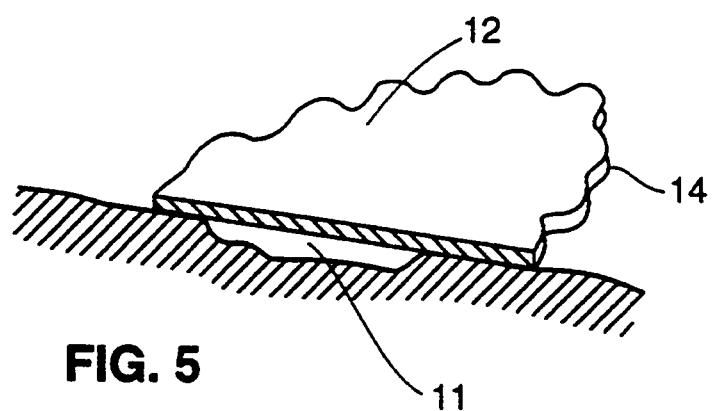
FIGS. 5 and 6 are sectional plan views of an alternative embodiment of the bandage assembly shown in FIGS. 1-4.
Figure 6:
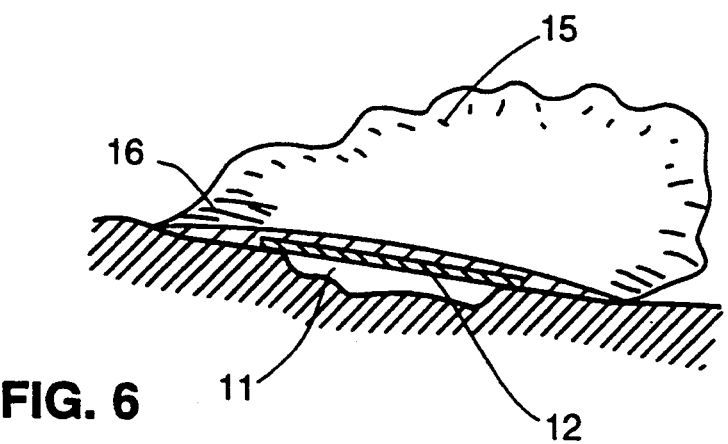

FIGS. 5 and 6 depict a second embodiment of the assembly. This second embodiment is identical to the embodiment shown in FIGS. 1-4 except for the configuration of the periphery of the segment of the adhesive tape. Specifically, the embodiment of FIGS. 1-4 has a regular-shaped periphery (i.e., the segment has a smooth oval shape) whereas the periphery of segment of tape of the embodiment of FIGS. 5 and 6 has an irregular curvilinear shape. It is believed that an irregular-shaped assembly is even less discernible than a regular-shaped assembly and may adhere better to curved surfaces of the skin. Of course, it is within the scope of the invention to use a tape segment of virtually any shape.

Figure 7:
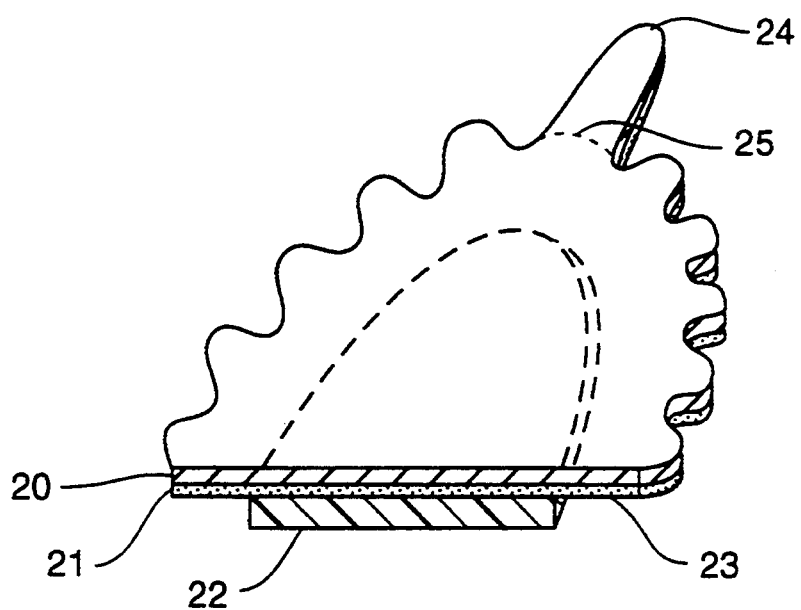
FIG. 7 is a sectional plan view of another embodiment of the invention.

FIG. 7 illustrates a preferred embodiment of a tape structure that is especially adapted to conceal a wound or blemish. The tape of FIG. 7 is a three layer laminate composed of an upper paper backing layer 20, an underlying pressure-sensitive adhesive layer 21, and a central wound release layer 22 made of a material such as polyurethane which does not adhere to wounds or blemishes. As shown, layer 22 is not coterminous in size with layer 21 so that a peripheral ring 23 of exposed adhesive surrounds layer 22. This ring provides the means by which the assembly is affixed to the skin. As further shown, the assembly has a scalloped edge and the backing is provided with a removable tab, 24 that facilitates its removal from a conventional release liner layer (not shown). The backing is scored at 25 across the neck of the tab to facilitate removal of the tab from the remainder of the tape.

The invention further concerns methods of bandaging or dressing wounds in a cosmetically acceptable fashion and of concealing unsightly dermatologic conditions, such as birthmarks, scars, keloids, allergic reactions, varicose veins, bruises among others. An exemplary method of this invention comprises applying an appropriate segment of adhesive tape according to this invention as described above to conceal the dermatologic condition, and then applying make-up to the top surface and periphery of the tape and the immediately adjacent skin wherein said make-up matches the skin tone of the individual and is applied in such a manner as to conceal the periphery of the tape.

This invention still further provides for methods of non-surgically lifting facial or other bodily wrinkles and sags of the skin. A representative example of such a method comprises applying an appropriate tape according to this invention, preferably paper tape, more preferably a micropore-type of paper tape just next to the hairline of an individual who desires a non-surgical face-lift in such a manner as to pull up the skin below the bandage so that the skin appears more taut and smooth than it had appeared. The make-up that matches the skin tone of the person undergoing the non-surgical face-lift is applied in a manner that causes the bandage to blend with the person's complexion. The invisibility of the tape can be enhanced by appropriate hair styling.

The kits of the invention will comprise in packaged combination: (1) one or more segments of adhesive tape that are adapted to be affixed to human skin, and (2) a container of make-up having a predetermined coloration. The kits may contain additional containers of make-up of various coloration. The segments may be of various precut sizes and shapes or be of one size that may be cut to the desired size and shape. The kits may also contain instructions for applying the tape and make-up to the skin.

The present invention is not to be considered limited in scope by the specific embodiments described above, since the described embodiments are intended only to be illustrative of particular aspects of the invention. Modifications of the above-described embodiments and modes for carrying out the invention that are obvious to those of skill in the medical and cosmetic arts are intended to be within the scope of the following claims.

I claim:

1. A bandage assembly for concealing a section of skin on a person comprising:
   (a) a segment of adhesive tape for attachment to (i) said section of skin and (ii) skin outwardly adjacent said section, said skin having a predetermined coloration, and said segment of tape having a top surface and a periphery; and
   (b) a layer of make-up having a coloration that matches the coloration of said skin, said layer covering said top surface and periphery of the tape and the skin outwardly adjacent said section of skin and said periphery, thereby concealing said section of skin and the segment of adhesive tape, said tape having a texture that retains the layer of make-up and a thinness that permits the assembly to blend with the skin at said periphery.

2. A bandage assembly according to claim 1 wherein the make-up is of a type selected from the group consisting of liquid, cream and stick types.

3. A bandage assembly according to claim 1 further comprising a layer of material which is air permeable but variably liquid permeable which layer is in direct contact with the skin, when the bandage is applied.

4. A bandage assembly according to claim 1 wherein said periphery has an irregular shape.

5. A bandage assembly according to claim 1 wherein the portion of said layer covering the skin outwardly adjacent said periphery angles downward from said periphery.

6. A bandage assembly according to claim 1 further comprising a layer of absorptive material which is applied to the surface of a wound.

7. A bandage assembly according to claim 6 further comprising a layer of material which is air permeable but variably liquid permeable which is between the tape and the layer of absorptive material.

8. A bandage assembly according to claim 1 wherein the adhesive tape is paper tape.

9. A bandage assembly according to claim 8 wherein the adhesive tape is a micropore-type of paper tape.

10. A bandage assembly according to claim 9 wherein the micropore-type of paper tape is a surgical tape which is tacky.

11. A bandage assembly according to claim 1 wherein said section of skin defines a wound or blemish and the adhesive tape comprises a laminated composite of a backing layer, an underlying pressure-sensitive adhesive layer, and a basal layer of a wound or blemish release material, said basal layer being smaller in area than the adhesive layer so that the adhesive layer provides an exposed peripheral ring about the basal layer.

12. A bandage assembly according to claim 11 further comprising a material which is air permeable but variably liquid permeable between the tape and the non-adhesive material.

13. A bandage assembly according to claim 11 further comprising an absorptive material between the tape and the wound or blemish release material.

14. A bandage assembly according to claim 13 wherein said absorptive material is surgical gauze.

15. A bandage assembly according to claim 13 further comprising in combination with said absorptive material a material which is air permeable but variably liquid permeable.

16. A bandage assembly according to claim 13 wherein said absorptive material is impregnated with a therapeutic agent.

17. A bandage assembly according to claim 16 wherein said therapeutic agent is selected from the group consisting of antibiotics, drying lotions, epidermal growth factors, steroids, hormones, and healing factors.

18. A method of concealing a section of skin on a person comprising
   (a) affixing a segment of adhesive tape to said section of skin and to skin which is outwardly adjacent said section of skin, said segment having a top surface and a periphery, and
   (b) covering the top surface and periphery of the segment of adhesive tape and the skin outwardly adjacent said section of skin and said periphery with a layer of make-up having a coloration that matches the coloration of the outwardly adjacent skin, said tape having a texture that retains the layer of make-up and a thinness that permits the make-up covered tape to blend with the skin at said periphery.

19. A kit for concealing a section of skin on a person comprising a packaged combination:
   (a) a container containing a flowable make-up whose coloration matches the coloration of the section of skin; and
   (b) a segment of adhesive tape that is sized and shaped to overlie said section, said tape having a top surface having a texture that allows the tape to retain said make-up when it is applied thereto and said tape having a thinness that permits the tape to blend with said section of skin when the tape is covered with a layer of the make-up.

* * * * *